US00PP36888P3

(12) United States Plant Patent
Hansen

(10) Patent No.: US PP36,888 P3
(45) Date of Patent: Aug. 12, 2025

(54) ***ARTEMISIA* PLANT NAMED 'SILVER LINING'**

(50) Latin Name: ***Artemisia ludoviciana* x *stelleriana***
Varietal Denomination: Silver Lining

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 154 days.

(21) Appl. No.: 18/445,325

(22) Filed: Jul. 11, 2023

(65) Prior Publication Data

US 2025/0024763 P1 Jan. 16, 2025

(51) Int. Cl.
*A01H 5/12* (2018.01)
*A01H 6/14* (2018.01)

(52) U.S. Cl.
USPC ..... Plt./373
CPC ..... *A01H 5/12* (2013.01); *A01H 6/14* (2018.05)

(58) Field of Classification Search
USPC ..... Plt./373
CPC ... A01H 5/12; A01H 5/00; A01H 6/12; A01H 6/14
See application file for complete search history.

(56) References Cited

PUBLICATIONS

Francis, Some of the newest perennials for 2023 (and 2022) . . . my choices amongst the clamouring hoards, retrieved on Feb. 11, 2025 at https://ailsa.substack.com/p/some-of-the-newest-perennials-for?utm_source=profile&utm_medium=reader2, 2022 pp. 1-17. (Year: 2022).*
Shultz, Artemisia, Treatment of Artemisia for the Flora of North America, v. 19, 2005, 7 pp. (Year: 2020).*

* cited by examiner

*Primary Examiner* — June Hwu

(57) ABSTRACT

The new and distinct cultivar of ornamental, hardy, Wormwood, *Artemisia* plant named 'Silver Lining' with a broad mounded habit of strong dense stems that remain upright through the growing season and do not open in the center of the plant. The new plant is vigorous with many large, durable, distally-lobed, broad, irregularly, and deeply dissected foliage of silver- white.

2 Drawing Sheets

Botanical classification: *Artemisia ludoviciana* x *stelleriana.*

Variety denomination: 'Silver Lining'.

STATEMENT REGARDING PRIOR DISCLOSURES UNDER 37 CFR 1.77(B)(6)

The claimed plant was first sold to BH Johnson Nursery on Jan. 30, 2023, by Walters Gardens, Inc., who obtained the plant and all information relating thereto, from the inventor. No plants of *Artemisia* 'Silver Lining' have been sold to the public or offered for sale in this country or anywhere in the world nor has any disclosure of the new plant been made more than one year prior to the filing date of this application, and such sale or disclosure within one year was either derived directly or indirectly from the inventor and would be considered a 35 U.S.C. 102(b) exception.

BACKGROUND OF THE INVENTION

The present invention relates to a new and distinct plant of Wormwood, botanically known as *Artemisia* 'Silver Lining', and will be referred to hereinafter also by its cultivar name 'Silver Lining' and the new plant. The new plant cultivar of *Artemisia* is a winter-hardy semi-woody perennial useful for landscaping purposes.

*Artemisia* 'Silver Lining' was hybridized by the inventor at a wholesale perennial nursery in Zeeland, Michigan on Jul. 1, 2019, between *Artemisia ludoviciana* 'Silver Queen' (not patented) as the female or seed parent and *Artemisia stelleriana* 'Silver Brocade' (not patented) as the male or pollen parent. The seed was collected on Aug. 18, 2019, and sown in late winter of 2020 at the same nursery in Zeeland, Michigan. The new plant was a single plant selected from among many seedlings and given the breeder code 19-1-6 during the evaluation process. *Artemisia* 'Silver Lining' was originally selected in the summer of 2020. All subsequent evaluations were performed in a full-sun trial garden at the same nursery with loamy sand soil and irrigation and fertilizer as required. The plant was propagated by stem cuttings at the same nursery in Zeeland, MI in 2020, and the original plant and the cuttings were evaluated over the next year until final approval for introduction in the summer of 2021. The resultant asexually propagated cuttings have been stable and identical to the original plant in successive asexual propagations.

SUMMARY OF THE INVENTION

*Artemisia* 'Silver Lining' differs from its parent as well as all other hardy Wormwood known to the inventor in a combination of traits. The following characteristics in combination distinguish 'Silver Lining' from all other *Artemisia* plants known to the inventor:

1. Broad mounded habit with strong dense stems;
2. Distally lobed leaves that are broadly, irregularly, and deeply dissected;
3. Silvery-white leaf and stem color;
4. Foliage is durable and the plant habit resists opening up later in the season;
5. Vigorous growth rate without invasive rhizomes.

The nearest comparison plants known to the inventor are: the parent plant *Artemisia gmelinii* 'Balfernlym' U.S. Plant Pat. No. 33,775, *Artemisia gmelinii* 'Balfernarc' U.S. Plant Pat. No. 33,774, *Artemisia* hybrid 'G18123' U.S. Plant Pat. No. 33,773, *Artemisia mauiensis* 'TNARTMS' U.S. Plant Pat. No. 30,968, and *Artemisia ludoviciana* 'Silver King' (not patented).

'Balfernlym' and 'Balfernarc' have foliage that is dark-green and medium-green, respectively, and both are more deltoid-shaped with finer dissected fem-like foliage. 'G18123' has narrower foliage that is less dissected and lobed. 'TNARTMS' has more linear-lobed foliage that is more arching and flexible, and the plant is not as winter hardy. The habit of 'Silver King' is taller, aggressively spreading by rhizomes, and with a tendency to lodge, and the foliage is narrower, more lanceolate, and less dissected.

The female parent, 'Silver Queen', has a more upright habit, narrower foliage that is more finely dissected, lobe apices are more acute, and it spreads aggressively by rhizomes. The male parent, 'Silver Brocade' has a lower mounded habit, the foliage is smaller and shorter with more rounded leaf lobes.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a plant grown in full sun field in loamy sand soil in trial gardens of a nursery in Zeeland, MI.

DETAILED BOTANICAL DESCRIPTION

Figure 1:
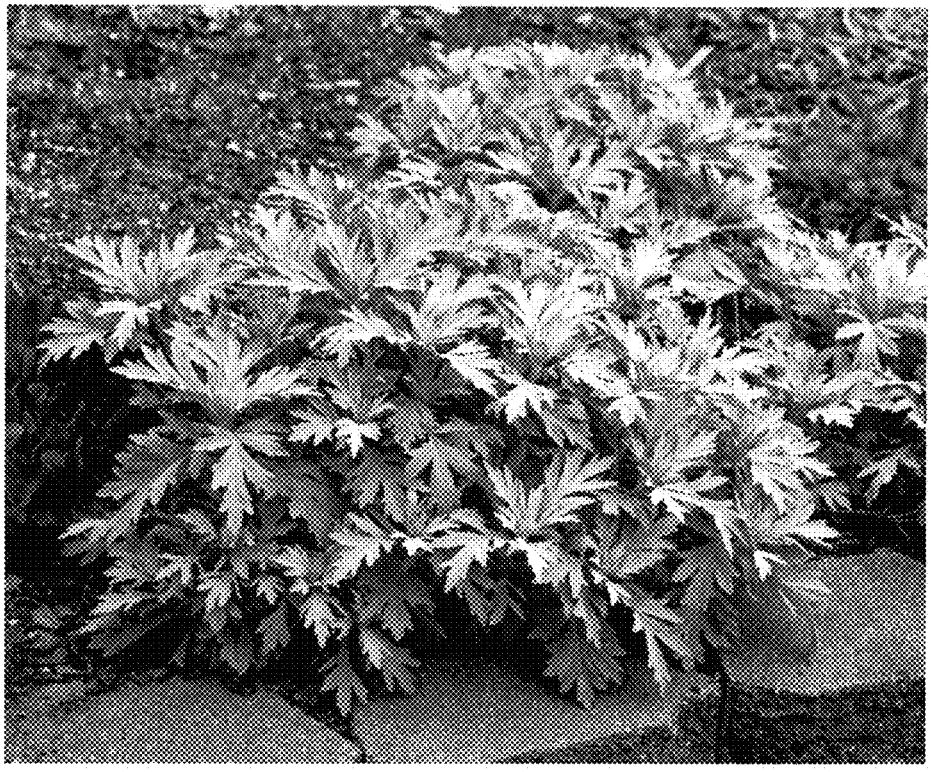
FIG. 1 shows the early summer habit of a two-year-old plant.
Figure 2:
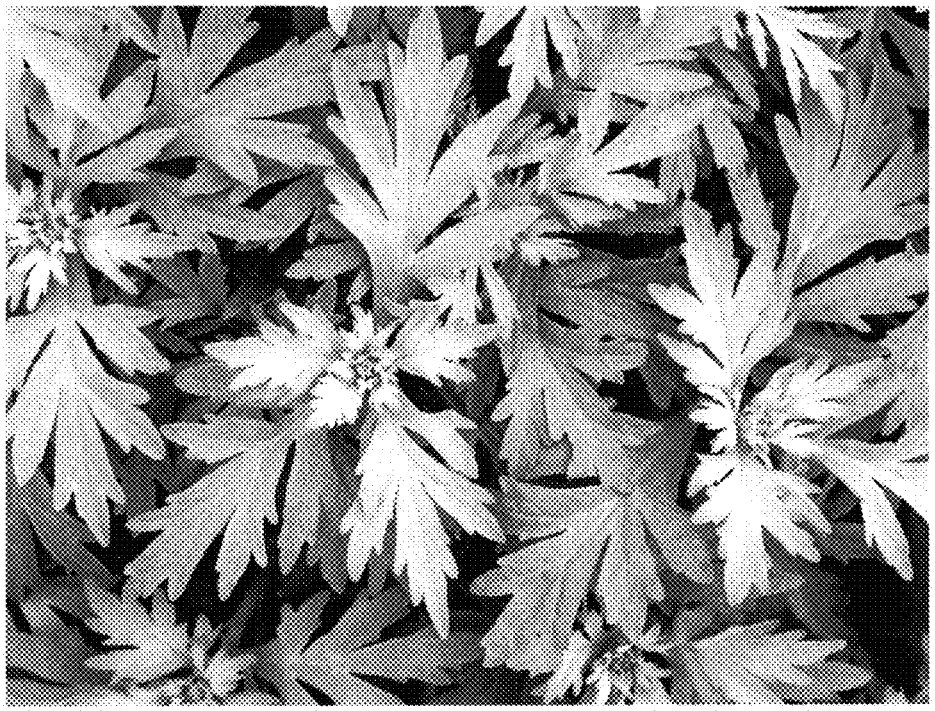
FIG. 2 shows a close-up of the foliage of a two-year-old plant.
Figure 3:
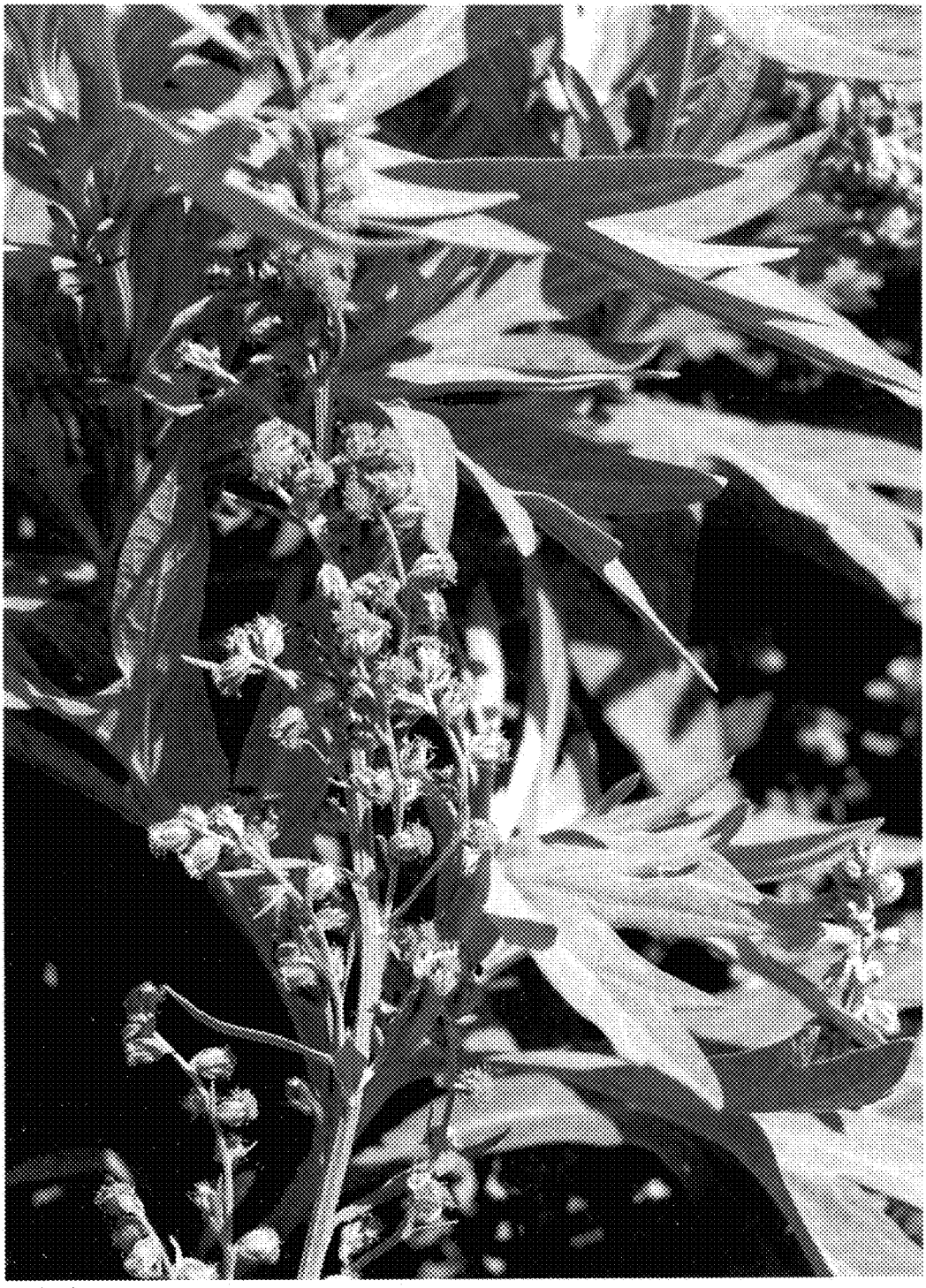
FIG. 3 shows a close-up of the flower stems of a three-year-old plant.

The following is a detailed description of *Artemisia* 'Silver Lining' as observed and compared to other cultivars for three years in trial gardens at a nursery in Zeeland, MI. The following description is of two-year-old and three-year-old plants of *Artemisia* 'Silver Lining' in a lightly shaded greenhouse and a full-sun trial garden in Zeeland, MI with limited irrigation as needed and without any pinching or plant growth regulators. The new plant has not been observed under all possible environments, and the phenotype may vary slightly with different environmental conditions, such as temperature, light, fertility, moisture, and maturity levels, but without any change in the genotype. The color descriptions are in accordance with the 2015 edition of The R.H.S. Colour Chart of The Royal Horticultural Society, London, England, except where common dictionary color terms are used.

Plant habit: Broad low-mounded, habit with strong dense stems; herbaceous winter-hardy perennial; becoming semi-woody with age;

Plant size: Foliage to about 40 cm in height and about 90 cm in width at the widest point about 10 cm above soil; flowering to about 65 cm tall;

Root description: Fine, well-branched, fibrous; color between RHS 158A and RHS 155B;

Propagation: Stem cuttings; root initiation occurs in about 14 days at a temperature of 25° C.;

Growth rate: Vigorous;

Crop time: About 8 to 10 weeks to produce a finished plant in a 3.8-liter pot from a rooted plug;

Stem description: Cylindrical; basally branched; young portions lanulose; average about 24 cm long and about 3.5 mm across near base; about 6 branches per stem; older stems becoming glabrous, fluted, and woody proximally, with base to about 9 mm diameter; with herbal fragrance;

Stem color: Young expanding nearest RHS N155A, mature between RHS 202D and RHS N189D, woody stems between RHS 166A and RHS 166B and nearest RHS 165D;

Internode length: About 1.0 cm long in middle, average about 7.5 mm long;

Internode color: Same as surrounding stem;

Branches: Cylindrical; mostly proximally and distally; farinose; lower branches about 28 cm long and about 4 mm diameter at base, upper branches about 18 cm long and about 2.5 mm diameter;

Branch color: Nearest RHS N155A young, mature between RHS 202D and RHS N189D;

Foliage description: Dextrorse; obovate; irregularly and deeply lobed; lobes with acute apices; attenuate base; margin entire; pannose to hoary on adaxial and densely hoary to pannose abaxial; with herbal fragrance; young foliage distally reduplicate; to about 28 per young stem and 60 per woody stem;

Leaf size: To about 124 mm long and about 85 mm wide past middle, average about 90 mm long and about 65 mm wide; lobes to about 45 mm long and 20 mm wide, average about 22 mm long and 12 mm wide;

Leaf color: Young adaxial proximally nearest RHS 192D, distal 2 mm apices nearest RHS 137C; young abaxial proximally nearest RHS 192D, distal 2 mm apices nearest RHS 192B; mature adaxial nearest RHS 136A with light tomentum of between RHS 192D to RHS NN155D; mature abaxial between RHS 191B and RHS 191C;

Leaf venation: Pinnate; adaxial lanulose and flat, and abaxial lanulose and costate; Vein color: adaxial nearest RHS 147B and abaxial nearest RHS 194C;

Petiole: Slightly concavo-convex, lanulose; sessile to about 3 mm long and about 3 mm across, average about 1.5 mm long and about 2.5 mm across at base;

Petiole color: Adaxial center nearest RHS 147B and margins nearest RHS 195C; between RHS 191B and RHS 191C;

Peduncle: Sessile for individual capitulum; attached directly to stem;

Pedicel: Not observed; Capitulescence: panicle-like; flowering to about 30 cm long and to about 8 cm across; base about 5 mm diameter; with about 30 branches to about 26 cm long and 1 mm diameter containing up to about 16 inflorescences per branch; entire stem with about 175 to 200 inflorescences; inflorescences only on overwintered plants, not considered an ornamental aspect of the new plant; flowering height about 65 cm;

Capitulescence stem color: Nearest RHS 189D;

Inflorescence buds about one day prior to opening: Fluted ellipsoidal; acute apex; rounded base; enclosed by involucre; about 4 mm long and about 3 mm diameter near middle;

Bud color: Nearest RHS 189D with phyllary midrib nearest RHS 141B;

Disk florets: Actinomorphic; rotate; to about 5 mm long and about 1 mm across at apex;

Inflorescence: Consisting of about 26 disk florets and no ray florets borne in capitulum; to about 5 mm long and 4 mm diameter near middle; central florets perfect, peripheral florets pistillate;

Capitulum attitude: Upwardly to slightly outwardly; Inflorescence fragrance: slight herbal;

Corolla: Tubular; to about 3 mm long and 1 mm across at apex;

Tepals: To about 3 mm long; fused in basal 2.5 mm; acute apex;

Tepal color: Adaxial and abaxial distal portion between RHS 2D and RHS 160D; adaxial and abaxial proximal portion nearest RHS N144D;

Gynoecium: One pistil; about 3.5 mm long;

*Style*.—About 1.5 mm long and about 0.3 mm diameter; color nearest RHS 145B.

*Stigma*.—Bifid in the terminal 0.5 mm, about 0.2 mm across; color nearest RHS 145B.

*Ovary*.—Oblong; about 1 mm long and 0.5 mm across; color nearest RHS 145C.

Androecium: Five; connate;

*Filaments*.—Cylindrical; short, straight; less than 0.5 mm long and about 0.1 mm diameter, color too small to determine.

*Anther*.—Five; connate; oblong; basifixed; longitudinal, about 1 mm long and 0.2 mm across, color nearest RHS 2C.

*Pollen*.—Not yet observed.

Involucre: Consisting of about two rows of phyllaries;

Phyllaries: Lanceolate; with acute apex and truncate base; arcuate around capitulum; lanulose; about 10 to 14 per capitulum; to about 2.5 mm long and 1 mm across at base;

Phyllaries color: Adaxial and abaxial nearest RHS 192D with adaxial midrib nearest RHS 141B;

Seed: Not yet observed;

Winter hardiness: At least to U.S.D.A. zone 4;

Growth: Highly resistant to drought once established; grows best in full sun;

Pest and disease resistance: Wormwood is typically resistant to deer and rodent browsing. No other susceptibility or resistance to diseases or pests has been observed except that which is common to *Artemisia*.

It is claimed:

1. A new and distinct cultivar *Artemesia* plant named 'Silver Lining' as herein described and illustrated.

* * * * *